(12) United States Patent
Todd et al.

(10) Patent No.: US 8,029,439 B2
(45) Date of Patent: Oct. 4, 2011

(54) DISPOSABLE ATTACHABLE LIGHT SOURCE UNIT FOR AN ENDOSCOPE

(75) Inventors: Erik F. D. Todd, Redwood City, CA (US); Hasan Ertas, Sunnyvale, CA (US); Andrew J. Hamel, San Mateo, CA (US)

(73) Assignee: Stryker Corporation, Kalamazoo, MI (US)

( * ) Notice: Subject to any disclaimer, the term of this patent is extended or adjusted under 35 U.S.C. 154(b) by 1310 days.

(21) Appl. No.: 11/179,161

(22) Filed: Jul. 11, 2005

(65) Prior Publication Data

US 2006/0173245 A1 Aug. 3, 2006

Related U.S. Application Data

(60) Provisional application No. 60/648,148, filed on Jan. 28, 2005.

(51) Int. Cl.
*A61B 1/06* (2006.01)

(52) U.S. Cl. ......... 600/178; 600/160; 362/572; 362/574

(58) Field of Classification Search .................. 600/160, 600/172, 175, 178–180, 182, 476; 362/555, 362/572, 574, 580
See application file for complete search history.

(56) References Cited

U.S. PATENT DOCUMENTS

| | | | |
|---|---|---|---|
| 3,042,022 A | 7/1962 | Sheldon | |
| 3,090,379 A | 5/1963 | Ferris et al. | |
| 4,406,280 A | 9/1983 | Upsher | |
| 4,433,675 A | 2/1984 | Konoshima | |
| 4,823,244 A * | 4/1989 | Alaybayoglu et al. | 362/194 |
| 5,363,135 A | 11/1994 | Inglese | |
| 5,363,839 A * | 11/1994 | Lankford | 600/112 |
| 5,371,384 A | 12/1994 | Wada | |
| 5,604,531 A | 2/1997 | Iddan et al. | |
| 5,743,848 A * | 4/1998 | Koeda et al. | 600/178 |
| 5,746,494 A * | 5/1998 | Koeda et al. | 362/560 |
| 5,908,294 A | 6/1999 | Schick et al. | |

(Continued)

FOREIGN PATENT DOCUMENTS

CA 2177178 6/1995

(Continued)

OTHER PUBLICATIONS

Pai Hsiang Wang et al., "Metal bonding delivers high-power AlGaInP-on-silicon LEDs," Compound Semiconductor magazine, pp. 1-4, downloaded from http://www.compoundsemiconductor.net/articles/magazine/8/12/2/1 on Jul. 19, 2004.

(Continued)

*Primary Examiner* — John P Leubecker
*Assistant Examiner* — Samuel Candler
(74) *Attorney, Agent, or Firm* — Blakely, Sokoloff, Taylor & Zafman LLP.

(57) ABSTRACT

An LED based light source unit for an endoscopic imaging system produces illumination for a camera through an endoscope. The light source unit includes an array of LEDs mounted to a thermally conductive substrate, a light guide to collect light emitted from the LEDs and to couple the light into a group of optical fibers within the endoscope, and an interface to allow the light source unit to be removably attached to the endoscope at the endoscope's external light port. The LEDs therein may be overdriven by power for increased light output. When the LEDs reach their lifetime, the light source unit can be discarded.

6 Claims, 15 Drawing Sheets

U.S. PATENT DOCUMENTS

| | | | |
|---|---|---|---|
| 5,999,749 | A | 12/1999 | Kobayashi et al. |
| 6,036,636 | A | 3/2000 | Motoki et al. |
| 6,095,970 | A * | 8/2000 | Hidaka et al. ............... 600/110 |
| 6,186,944 | B1 | 2/2001 | Tsai |
| 6,190,309 | B1 | 2/2001 | Ooshima et al. |
| 6,217,512 | B1 | 4/2001 | Salo et al. |
| 6,260,994 | B1 | 7/2001 | Matsumoto et al. |
| 6,318,887 | B1 | 11/2001 | Matsumoto |
| 6,331,156 | B1 | 12/2001 | Haefele et al. |
| 6,413,207 | B1 | 7/2002 | Minami |
| 6,449,006 | B1 | 9/2002 | Shipp |
| 6,474,836 | B1 | 11/2002 | Konagaya |
| 6,479,942 | B2 | 11/2002 | Kimura |
| 6,488,619 | B1 | 12/2002 | Miyanaga |
| 6,533,722 | B2 | 3/2003 | Nakashima |
| 6,551,240 | B2 | 4/2003 | Henzler |
| 6,554,765 | B1 * | 4/2003 | Yarush et al. ............... 600/132 |
| 6,644,837 | B2 | 11/2003 | Borders et al. |
| 6,656,112 | B2 | 12/2003 | Miyanaga |
| 6,796,939 | B1 * | 9/2004 | Hirata et al. ............... 600/179 |
| 6,921,920 | B2 | 7/2005 | Kazakevich |
| 6,964,501 | B2 * | 11/2005 | Ryan ............... 362/294 |
| 7,041,054 | B2 * | 5/2006 | Klootz ............... 600/178 |
| 7,345,312 | B2 * | 3/2008 | Kazakevich ............... 257/81 |
| 7,355,155 | B2 | 4/2008 | Wang |
| 7,433,589 | B2 | 10/2008 | Odaka |
| 7,491,165 | B2 * | 2/2009 | Kogasaka et al. ............... 600/104 |
| 7,668,450 | B2 | 2/2010 | Todd et al. |
| 2002/0056804 | A1 | 5/2002 | Konagaya |
| 2003/0018238 | A1 * | 1/2003 | Obata et al. ............... 600/179 |
| 2003/0042493 | A1 * | 3/2003 | Kazakevich ............... 257/98 |
| 2003/0147254 | A1 * | 8/2003 | Yoneda et al. ............... 362/551 |
| 2003/0156430 | A1 | 8/2003 | Ota et al. |
| 2004/0120162 | A1 * | 6/2004 | Tsimerman et al. ............... 362/573 |
| 2004/0240866 | A1 | 12/2004 | Ramsbottom |
| 2005/0231983 | A1 * | 10/2005 | Dahm ............... 362/800 |
| 2006/0020308 | A1 * | 1/2006 | Muldner ............... 607/88 |
| 2006/0022582 | A1 * | 2/2006 | Radkov ............... 313/503 |
| 2006/0069314 | A1 | 3/2006 | Farr |
| 2006/0120706 | A1 | 6/2006 | Cho et al. |

FOREIGN PATENT DOCUMENTS

| | | |
|---|---|---|
| DE | 19936958 A1 | 3/2001 |
| JP | 2005177134 A * | 7/2005 |

OTHER PUBLICATIONS

"Substrate solves power LED thermal problems," pp. 1-2, TT Electronics Welwyn Components, downloaded from http://www.electronicstalk.com/news/wel/well21.html on Jul. 19, 2004.

Restriction Requirement for U.S. Appl. No. 11/179,113, mailed Mar. 31, 2008, 5 pages.

Notice of Non-Compliant Amendment for U.S. Appl. No. 11/179,113, mailed Jun. 4, 2008, 3 pages.

Office Action for U.S. Appl. No. 11/179,113, mailed Oct. 16, 2008, 10 pages.

Final Office Action for U.S. Appl. No. 11/179,113, mailed Apr. 30, 2009, 7 pages.

* cited by examiner

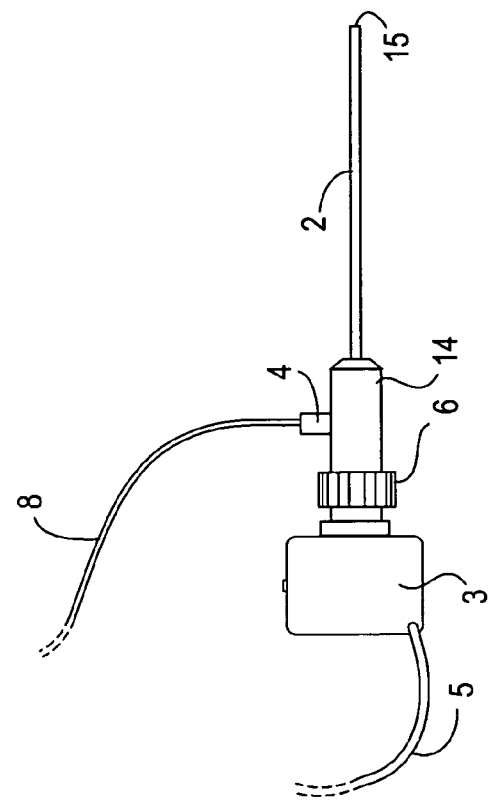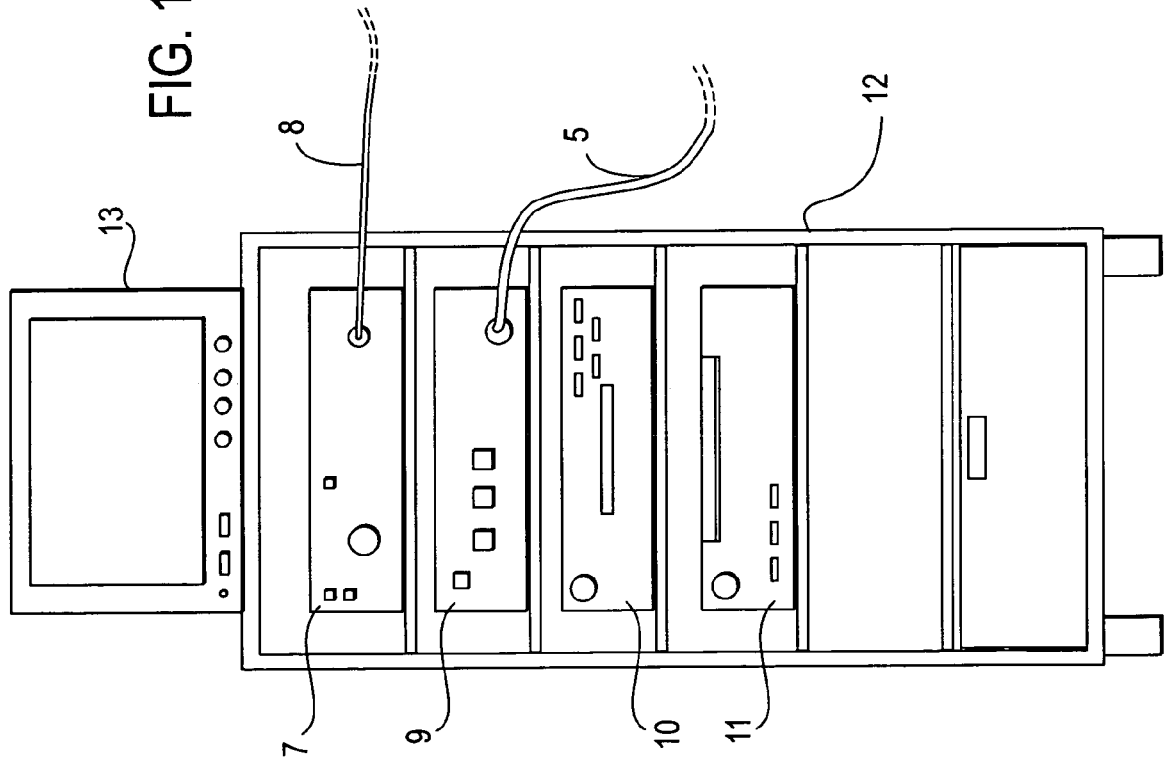

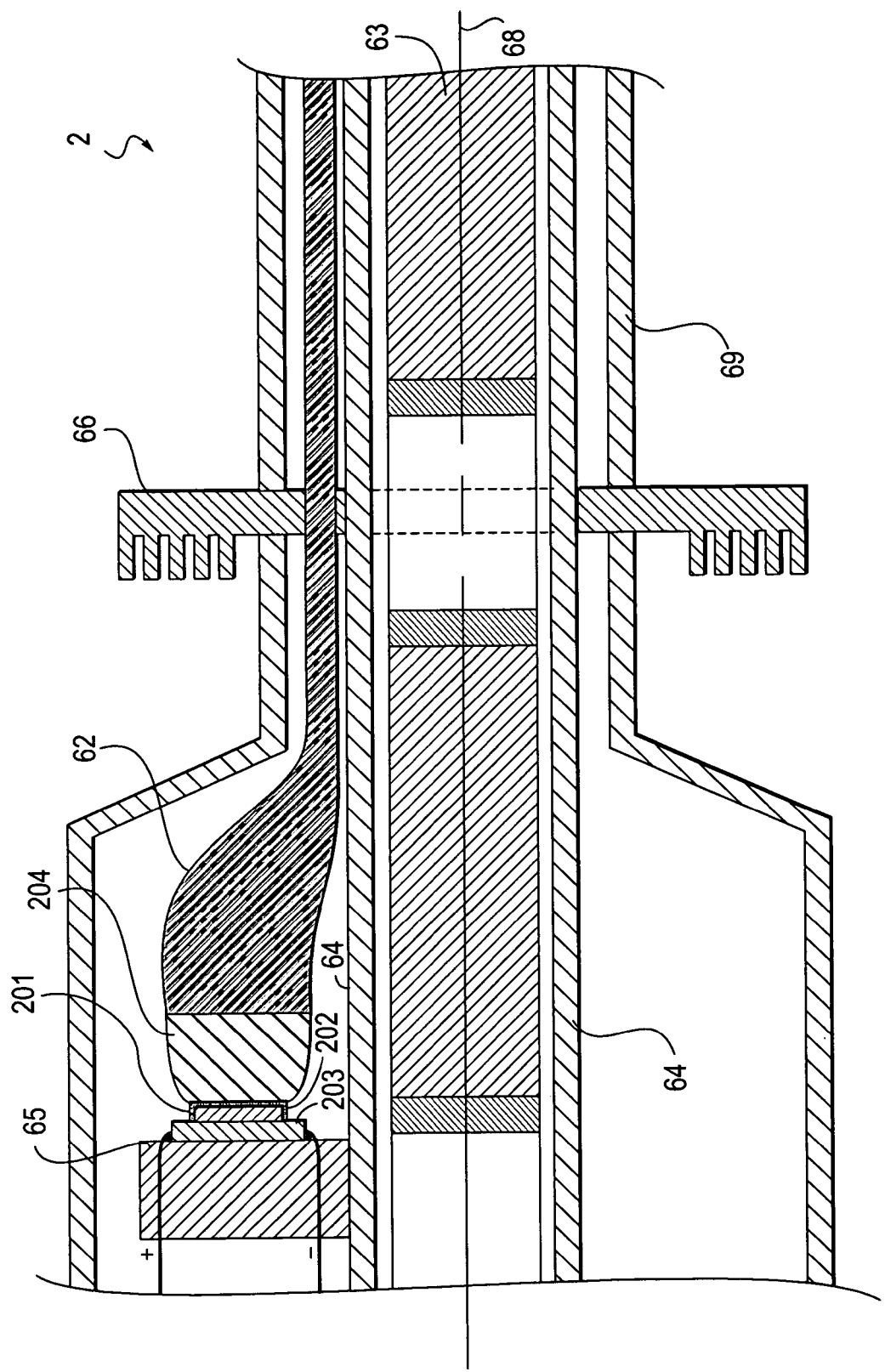

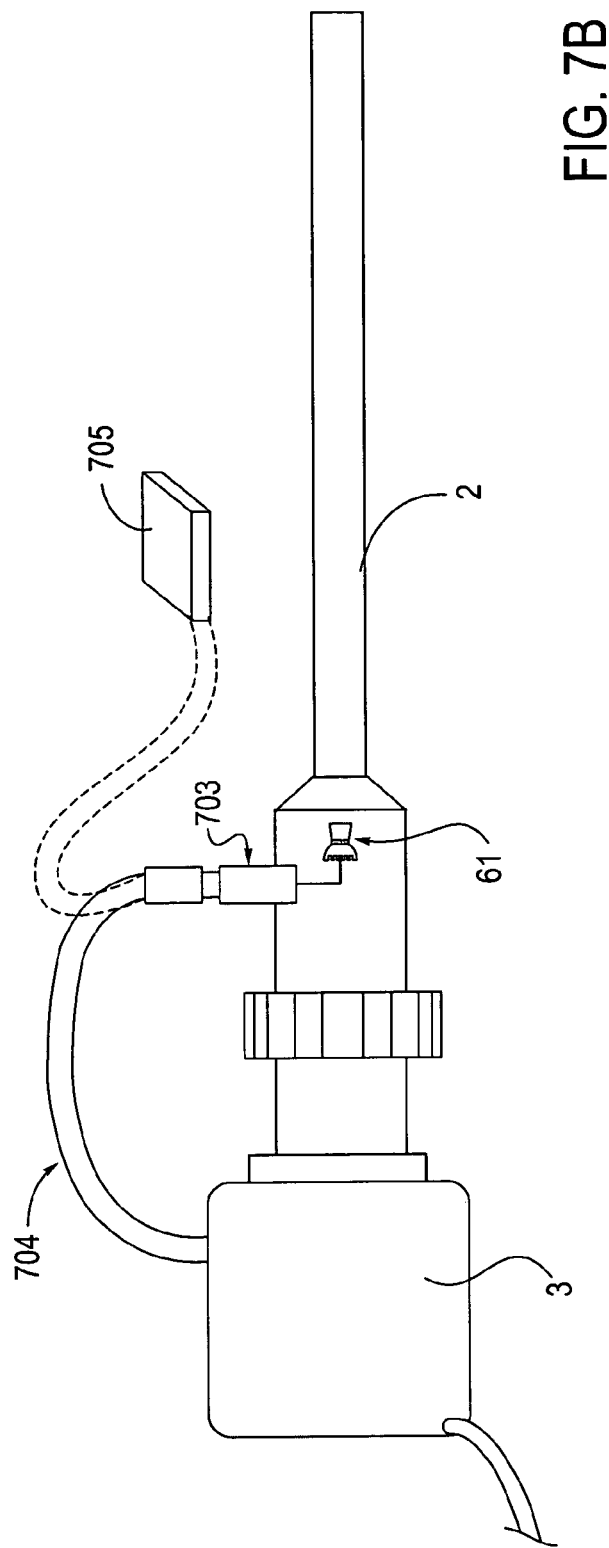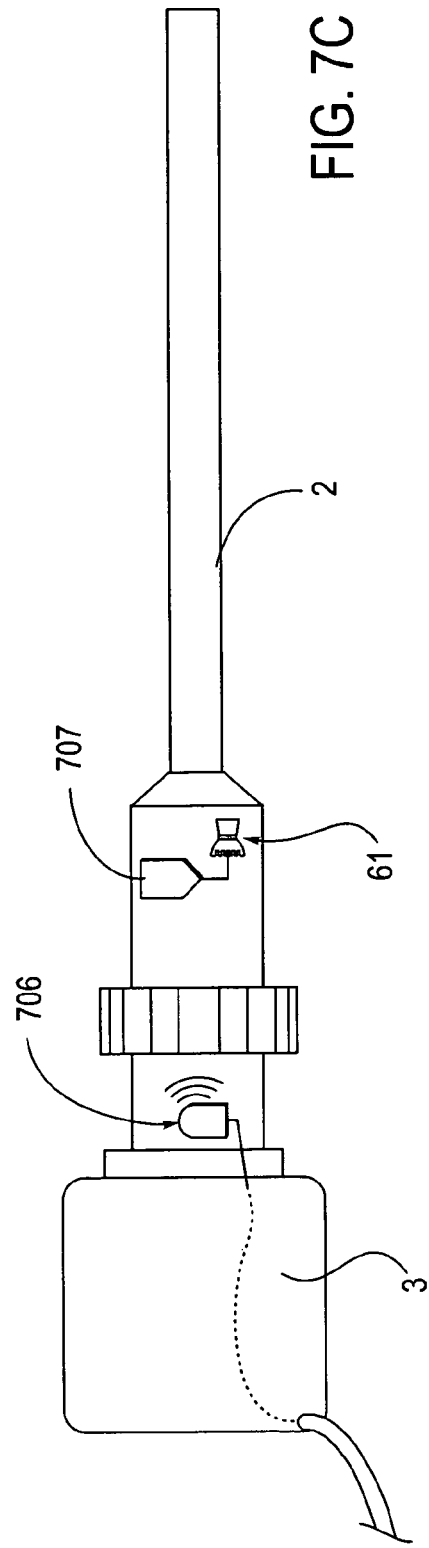

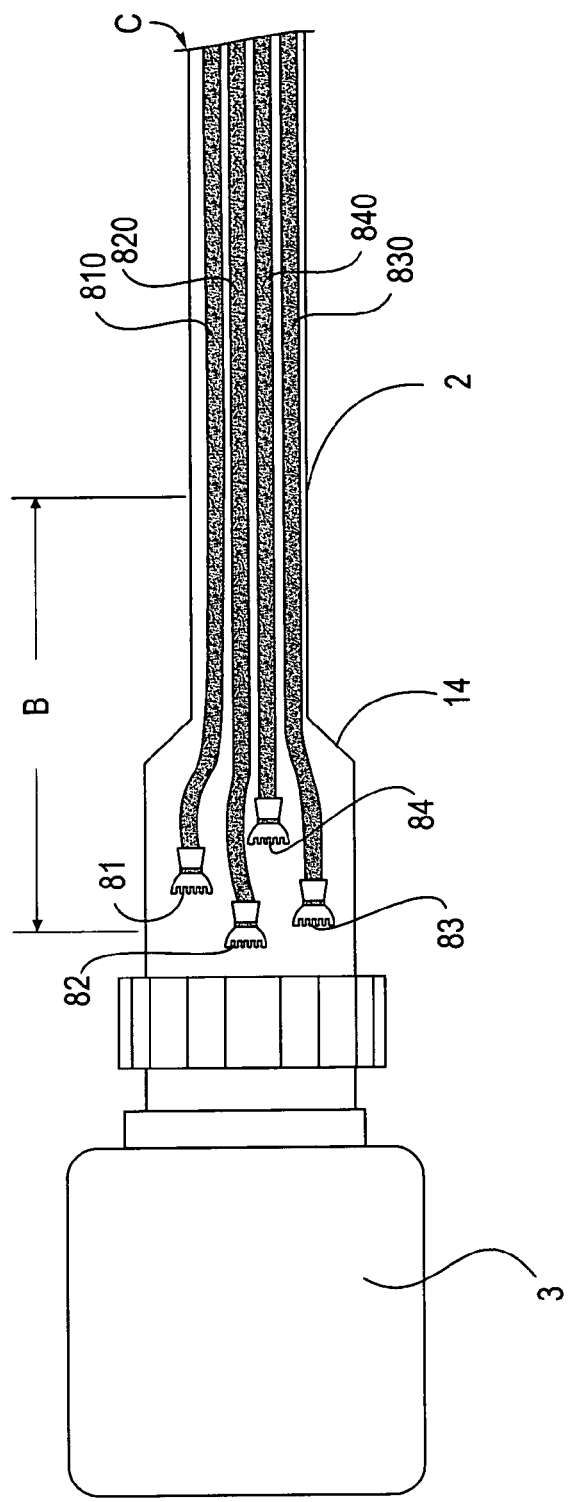
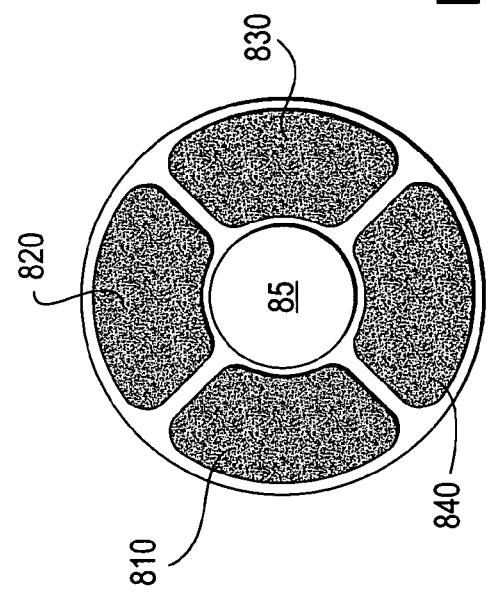
FIG. 8A
FIG. 8B

DISPOSABLE ATTACHABLE LIGHT SOURCE UNIT FOR AN ENDOSCOPE

This application claims the benefit of U.S. Provisional Patent application No. 60/648,148, filed on Jan. 28, 2005 and entitled, "Endoscopes with Disposable Attachable Light Source Unit and/or Integrated Light Source Unit," which is incorporated herein by reference.

RELATED APPLICATION

This application is related to co-pending U.S. patent application Ser. No. 11/179,113, filed concurrently herewith and entitled, "Endoscope with Integrated Light Source".

FIELD OF THE INVENTION

The present invention relates to a light source unit for an endoscopic imaging system, and more particularly, to an LED based light source unit ("LED light source unit") that can be removably coupled to an endoscope.

BACKGROUND

Endoscopy in the medical field allows internal features of the body of a patient to be viewed without the use of traditional, fully-invasive surgery. FIGS. 1A and 1B collectively illustrate an endoscopic imaging system such as commonly used in the medical field. FIG. 1A generally illustrates the image generation and display components of the system, while FIG. 1B illustrates the data acquisition components of the system. The data acquisition components include an endoscope 2, a camera 3, and a coupler 6. The endoscope 2 has a distal end, i.e., the tip of the scope shaft 15, and a proximal end, i.e., the housing 14, which is connected to the camera 3 by the coupler 6. The camera 3 acquires color video image data of internal features of a body through an optical pathway (a system of lenses, for example) in the endoscope 2. FIG. 1A shows the image generation and display components of the system, which include a camera control unit (CCU) 9, a light source unit 7, a monitor 13, a video recorder 10, and a printer 11, which are stored on a mobile cart 12. Various other system configurations are also possible.

High-intensity light is provided to the endoscope 2 by the light source unit 7 through a flexible light conduit 8, which may be a fiber optic cable. An external light port (e.g., light post 4) that extends from the housing 14 of the endoscope 2 enables the light conduit 8 to attach to the endoscope 2. Certain camera functions can be controlled from the camera control unit (CCU) 9. The camera 3 is coupled to the camera control unit (CCU) 9 by a flexible transmission line 5. The transmission line 5 conveys power to the camera 3, video image data from the camera 3 to the CCU 9, and various control signals bi-directionally between the camera 3 and the CCU 9. Image data received by the CCU 9 from the camera 3 are processed and converted to video images by the CCU 9, which are displayed on the monitor 13, and if desired, recorded by the video recorder 10 and/or used to generate static images that can be printed by printer 11.

A typical light source unit 7 is comprised of a light bulb, a ballast power supply, control circuitry and cooling fans. This system is extremely inefficient and must generate extremely bright light to compensate for the distance the light rays must travel and the losses experienced through the system. This system may also cause infrared heat energy to be transmitted into the patient, which can create hazardous conditions during the surgery. Furthermore, the color content of the light cannot be controlled, which can adversely affect image quality, and the light cable that connects the light source to the scope is cumbersome.

Using light emitting diodes (LEDs) as a light source for an endoscope has been proposed. Because LEDs are small in size, they can be integrated into an endoscope to bring the light source closer to the surgical site.

For example, there are proposals to place multiple LEDs as a light source into the tip or annular area of the scope shaft of an endoscope. There are, however, at least two problems with this kind of design. First, the space inside the tip or annular area of the scope shaft is relatively small. Therefore, very few LEDs can be integrated into the endoscope. Second, because endoscopes can come in different sizes, an LED based light source must be specifically designed for a particular endoscope size if it is placed in the tip or annular area of the scope shaft.

Current LEDs available are usually pre-packaged single diode assemblies. It is difficult to obtain the light output required for endoscopic applications in a compact space, as the packaging is often on the order of 50× the size of the LED. If multiple LEDs are placed on one circuit board, their proximity becomes limited by required heat dissipation. As heat increases, lifetime of the LED dramatically decreases. Reducing the supplied power can reduce the thermal load, but decreases the light output.

Also, different doctors prefer different color temperatures for illumination during an endoscopic procedure. It is desirable to have a light source unit that allows a doctor to adjust the color temperature of its light to the doctor's preferred condition during an endoscopic procedure. In addition, at a surgical site within a patient's body, some anatomical surfaces may be closer to the endoscope tip, where light is emitted, than other surfaces; as such, some portions of the image may become overly bright or overly dark. What is needed, therefore, is a light source unit for an endoscopic imaging system, which overcomes these problems.

SUMMARY OF THE INVENTION

The present invention includes a light source unit for an endoscopic imaging system. The light source unit includes an array of light-emitting elements mounted to a substrate, to produce illumination through an endoscope for a camera, an interface to allow the light source unit to be removably mounted to an external light port of the endoscope, and a light guide to collect light emitted from the light-emitting elements and to couple the light to the external light port.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which:

FIG. 1 illustrates an endoscopic imaging system;

FIG. 6C shows a close up cross-sectional view of section B of FIG. 6A, for an embodiment in which the substrate is coupled to a heat pipe integrated within the endoscope;

FIG. 7B illustrates a configuration to supply power via a cable from a camera to an LED light source unit integrated into an endoscope;

FIG. 7C illustrates a configuration to supply power wirelessly from a camera to an LED light source unit integrated into an endoscope;

FIG. 8A shows an arrangement of multiple LED light source units integrated into an endoscope;

FIG. 8B shows a close up view of the tip of the endoscope shown in FIG. 8A;

DETAILED DESCRIPTION

Figure 2:
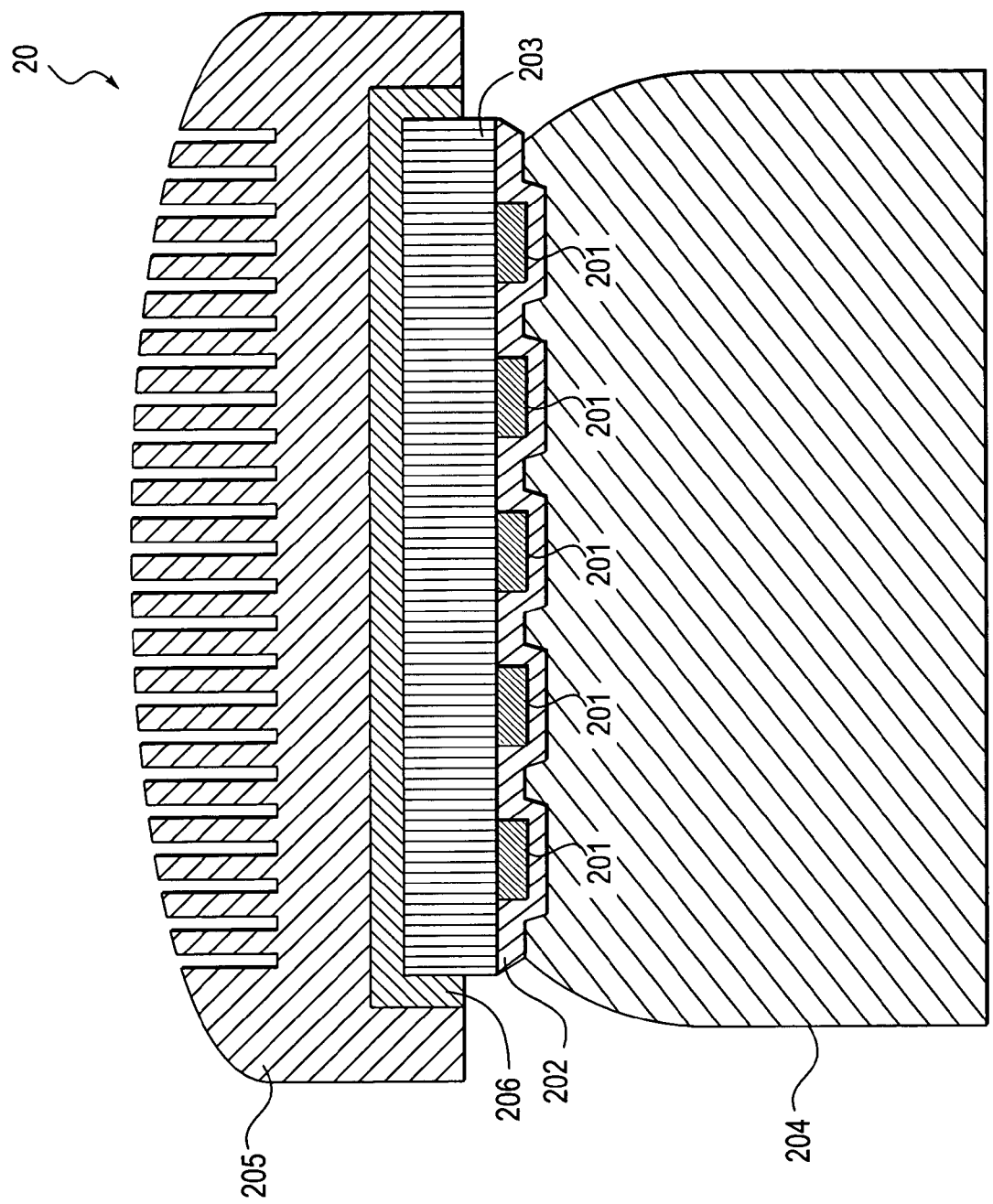
FIG. 2 shows an LED light source unit in a cross-sectional view.

An LED light source unit for an endoscopic imaging system is described. Note that in this description, references to "one embodiment" or "an embodiment" mean that the feature being referred to is included in at least one embodiment of the present invention. Further, separate references to "one embodiment" in this description do not necessarily refer to the same embodiment. Thus, the present invention can include any variety of combinations and/or integrations of the embodiments described herein.

As described in greater detail below, an LED based light source unit may include an array of LEDs mounted to a thermally conductive substrate, to increase the number of LEDs used while reducing the overall size of the light source unit, and while allowing for sufficient heat dissipation. To further improve heat dissipation, the substrate is mounted to a heat sink or heat pipe.

Although the embodiments described herein are based on the use of LEDs, it may be possible to replace the LEDs in the light source unit with another type of light-emitting element, such as incandescent or fluorescent lamps, nanotechnology diodes, bioflourescent/bioluminescent materials, etc. Although those other lighting technologies are not currently believed to be as suitable as LEDs for the embodiments of the invention described herein, it is conceivable that future developments in those technologies might make them more suitable for use in embodiments of the invention. Furthermore, it should be understand that use of the term "LED" in this description is not necessarily limited to conventional LEDs, and may encompass, for example, organic LEDs (OLEDs) or other types of LEDs.

In one embodiment, the LED light source unit may be removably coupled to an endoscope at the endoscope's external light port (e.g., light post) and can work with a variety of different endoscope sizes, produced by various endoscope manufacturers. Light produced by the light source unit is optically coupled at the endoscope's external light port into a group of optical fibers within the endoscope and is directed to the tip of the endoscope by these optical fibers.

LEDs work best on a specific amount or range of current, which is specified by the manufacturer. Pushing more current through them will produce more light, but also will produce more heat that can damage the LEDs; this usage mode is called "overdrive". In the prior art, LEDs are powered within their recommended operating range to protect against premature failure. The light source unit introduced herein can be operated in overdrive, so as to increase light output at the expense of the LEDs' lifetime in order to compensate for limited number of LEDs that can fit into a given package and the losses of light caused by a less efficient coupling system. When the LEDs reach their lifetime, the light source unit can then simply be discarded. Note that with the development of technology in the future, an LED array may produce sufficient light to overcome the less efficient coupling system without sacrificing lifetime, or there may be substantial improvement on the coupling system's efficiency. In that case, overdriving is not necessary.

The light source unit introduced above may include batteries to supply power to its LEDs. This design eliminates the need for a cable and allows the unit to be entirely sealed for sterilization. The light source unit may also or instead receive power via a cable from a camera coupled to an endoscope, as the camera already has DC power required to power its imaging detector, e.g., the CCD arrays. Powering the light source unit from this same source eliminates redundant power lines running through the operating room as well as reducing the length of the cable, in contrast with powering the light source unit via a more remote device.

In another embodiment, the LED light source unit is integrated into the housing of an endoscope. This light source unit couples directly to a group of optical fibers (or other non-imaging optical pathway) that run to the tip of the endoscope, and provides illumination to the surgical site. The losses which the light is subject to in the endoscope are smaller in this embodiment, requiring a smaller light source unit. As will be discussed in detail below, the light source unit may receive power from a battery pack via a cable, or receive power wirelessly or via transmission line from a camera coupled with the endoscope, for example.

A typical endoscope has optical fibers running to the tip of the endoscope. These fibers all meet back at the external light port (e.g., light post), where in prior art implementations they receive light via a light cable. In one embodiment of the invention, an endoscope may contain multiple (four, for example) LED light source units integrated into the housing of the endoscope. In such an embodiment, each of the light source units couples directly to a different corresponding group of optical fibers (or other non-imaging optical pathway) that directs the light to a distinct section of the tip of the endoscope. By being able to control light emitted from different regions around the periphery of the scope tip, it is possible to control light output into different regions of a surgical site. Since one region may contain surfaces that are closer to the endoscope tip than others, some portions of the image may become overly bright or overly dark. With regional control, the image illumination can be more evenly distributed.

White light can be produced by combining red, green, and blue LEDs together or by coating blue LEDs with a layer of phosphor that absorbs a proportion of the blue light emitted by the LEDs. Red LEDs may be added to an array of blue LEDs to improve the color rendering in the red side of the spectrum. The red LEDs are controlled separately from the blue LEDs so that the relative amount of red light with respect to blue can be increased or decreased. This design has the functional result of changing the perceived color temperature of the light produced by the light source unit. Bluer light is considered "colder" and redder light is considered "warmer". Because different doctors prefer different color temperatures when viewing different surgical sites within a patient's body, a doctor can adjust the color temperature of the light source unit to his/her preferred condition. Note that this color temperature control mechanism may be accomplished by combinations of LEDs of other colors, although a combination of blue LEDs and red LEDs is described here. In any event, this description does not limit the present invention to any specific color combination.

FIG. 2 shows an LED light source unit in a cross-sectional view. The LED light source unit 20 includes an array of LEDs 201 mounted to a thermally conductive substrate 203, which contains electrical traces used to supply power to the LEDs 201. The substrate can be made of conventional printed circuit board (PCB) material(s) designed for efficient heat dissipation (e.g., the substrate may contain embedded heat conductive material, such as copper), and can be manufactured by using, for example, Low Temperature Co-fired Ceramic (LTCC) technique. The substrate 203 is then mounted to a peltier device 206, a solid-state device also known as thermoelectric (TE) module that functions as a heat pump to move heat from one side of the device to the other. The peltier device 206 moves the heat from its side where the substrate 203 is mounted to the other side where a heatsink 205 is coupled. The thermally conductive substrate 203, the peltier device 206, and the heatsink 205 help to dissipate heat produced by the LEDs 201, reducing the LEDs' junction temperature, and improving the LEDs' lifetime.

In order to produce white light, the LEDs 201 may be a combination of red, green, and blue LEDs, or an array of blue LEDs coated with a layer of phosphor 202 that absorbs a proportion of the blue light emitted by the LEDs. A light guide 204, which can be a compound parabolic collector (CPC), collects light from the LEDs 201 with a broad emission angle, filtered through the phosphor layer 202, and couples the light along a more confined angle into optical fibers within an endoscope for high quality light transmission. The optical fibers then direct the light to the tip of the endoscope.

Figure 3A:
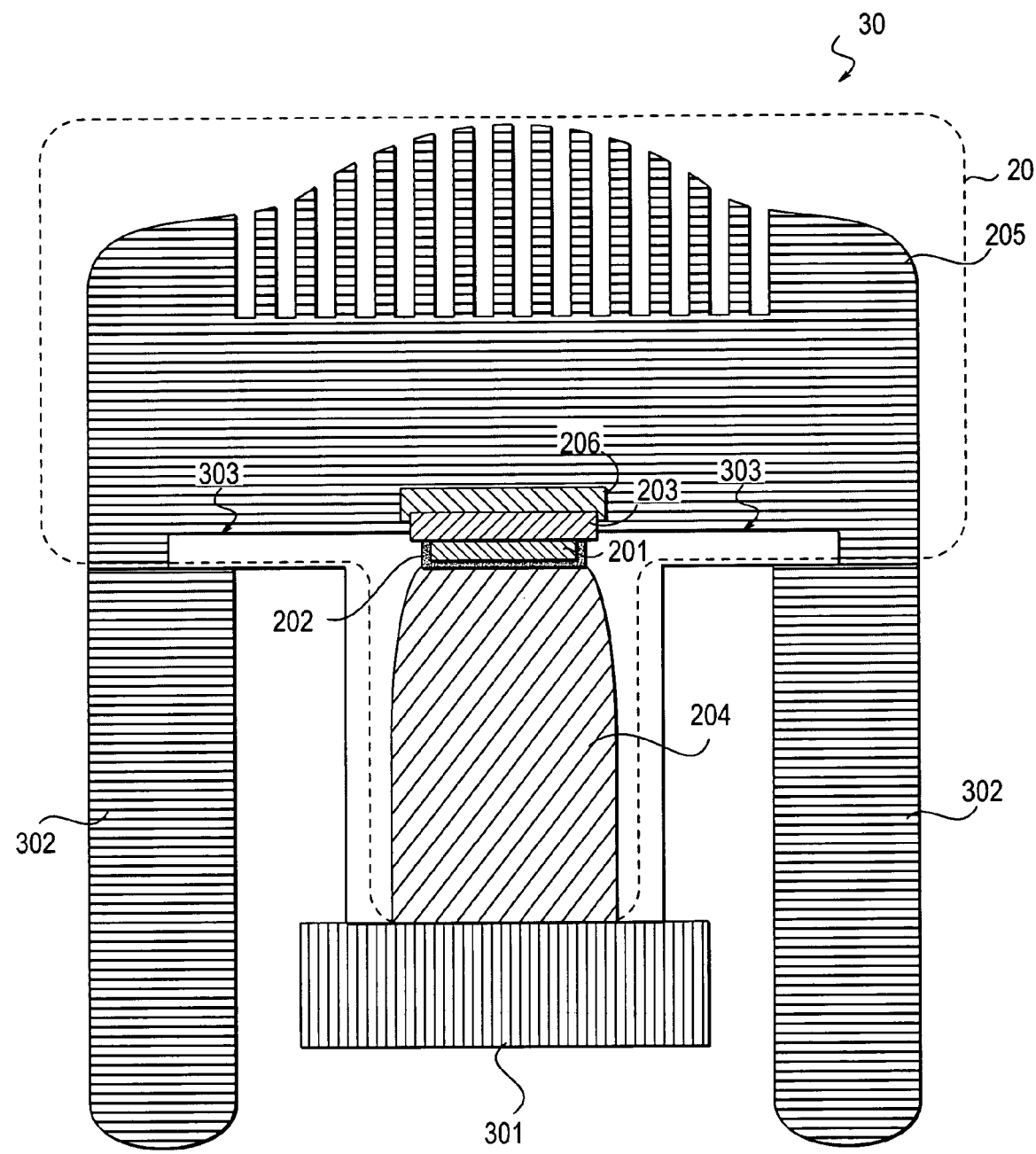
FIG. 3A is a cross-sectional view of an LED light source unit, which is powered by batteries and which may be removably coupled to an endoscope.

FIG. 3A is a cross-sectional view of an LED light source unit, which, according to one embodiment of the invention, is powered by batteries and may be removably coupled to an endoscope. As shown, the light source unit 30 includes essentially the same components as the LED light source unit 20 (FIG. 2). In addition, the light source unit 30 has an interface to enable the light source unit 30 to be coupled to an external light port (e.g., light post 4) of an endoscope. In the illustrated embodiment, the interface is an external coupler 301. In another embodiment, however, the interface could be integrated into the light source unit 30. Also as shown, the light source unit 30 has two battery compartments 302 to hold batteries for supplying power to the LEDs through the power lines 303. Batteries of conventional size and type, such as AA or other form factors of primary or secondary batteries, may be used, although customized batteries may provide better performance. In one embodiment, power is supplied to overdrive the LEDs for increased light output at the expense of shortened lifetime. This compensates for the limited number of LEDs that can fit into a given package and the inefficient coupling system.

Figure 3B:
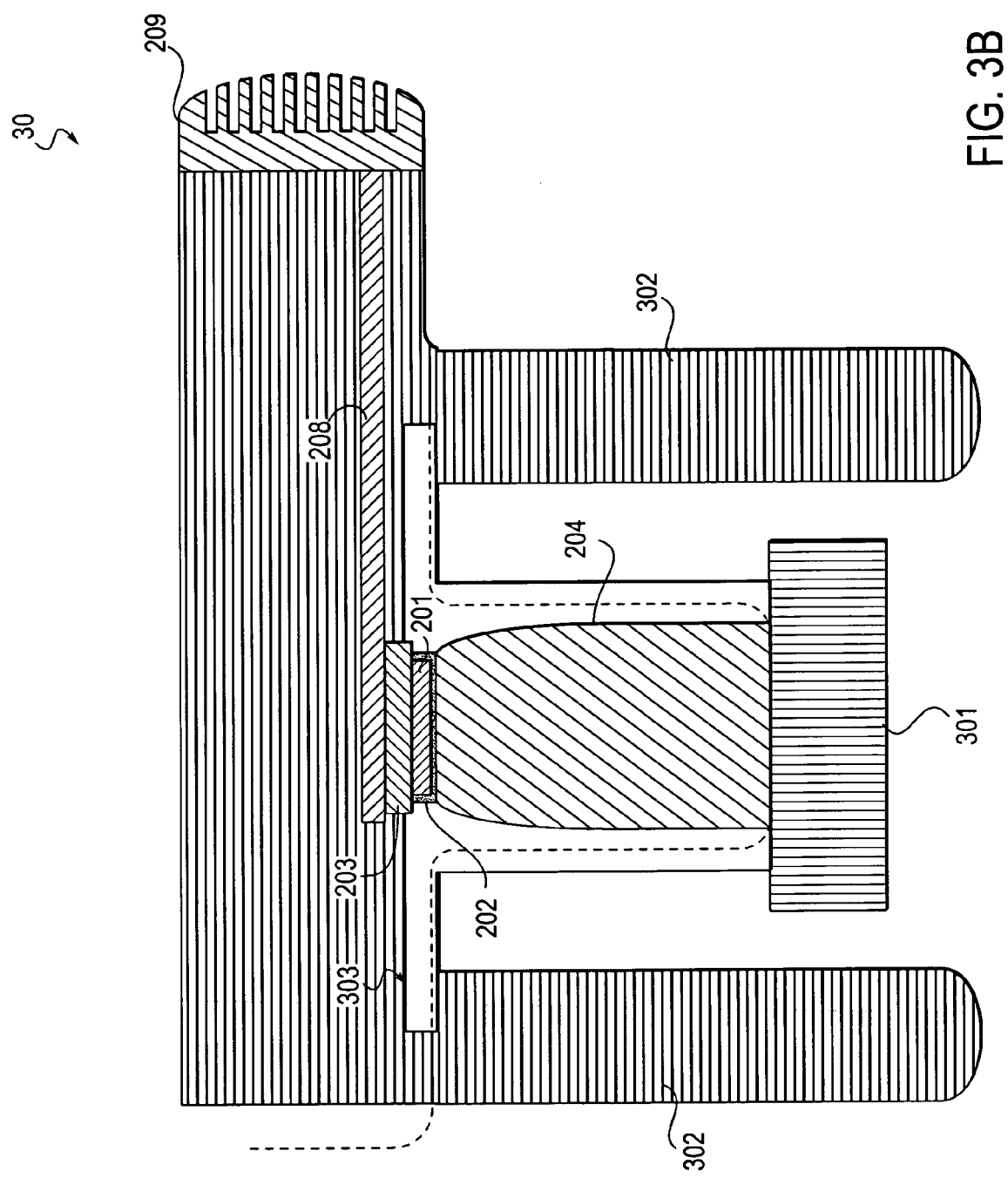
FIG. 3B is a cross-sectional view of an LED light source unit according to another embodiment, in which a heat pipe is used to connect the substrate to a heat sink.

A heat pipe can be used to provide more flexibility in the design of the location of the heat sink on the light source unit. For example, FIG. 3B shows the light source unit 30 according to another embodiment of the invention, in which a heat pipe 208 is used to couple the substrate 203 (physically and thermally) to a heat sink 209. The heat pipe 208 may be, for example, a hollow metal tube filled with alcohol or another liquid.

Note that various details can be altered from what is shown in FIGS. 3A and 3B. For example, the number, size, and shape of the battery compartment(s) and the way the compartment(s) integrate(s) with the light source unit may change depending on various considerations and design preferences. The idea, however, is to eliminate bulky power cables and make the endoscope more flexible. Therefore, the embodiments shown in FIGS. 3A and 3B do not limit the present invention in any specific way of design.

Figure 4A:
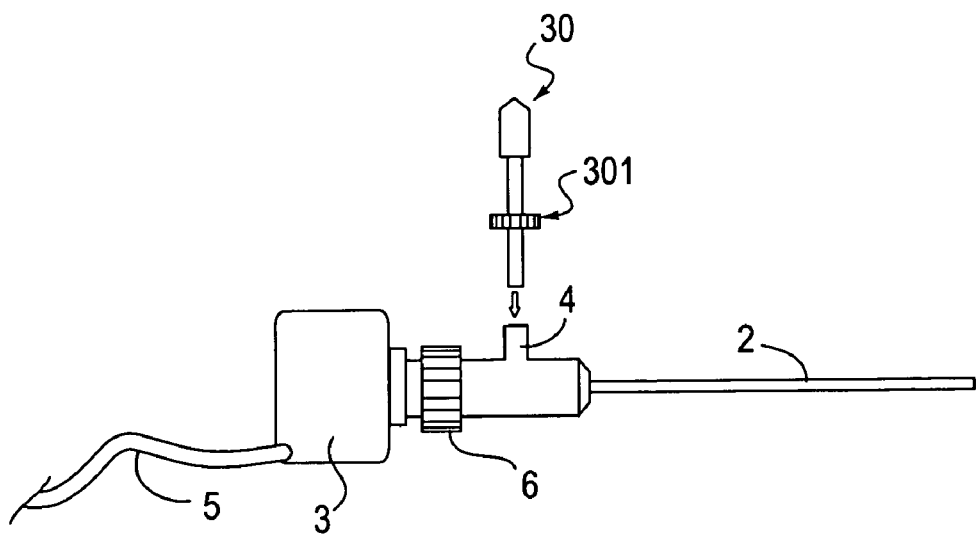
FIG. 4A shows a side view of an LED light source unit as described in FIG. 3 and an endoscope before the LED light source unit is connected to the endoscope.

FIG. 4A shows a side view of an LED light source unit, such as the one described in FIG. 3A, and an endoscope before the LED light source unit is connected to the endoscope. As shown, the light source unit 30 is going to be connected with the endoscope 2 by the coupler 301 at the light post 4. One of the advantages of such design is that the same light source unit can work with endoscopes with different size as long as the coupler 301 may connect with the external light port of the endoscope.

Figure 4B:
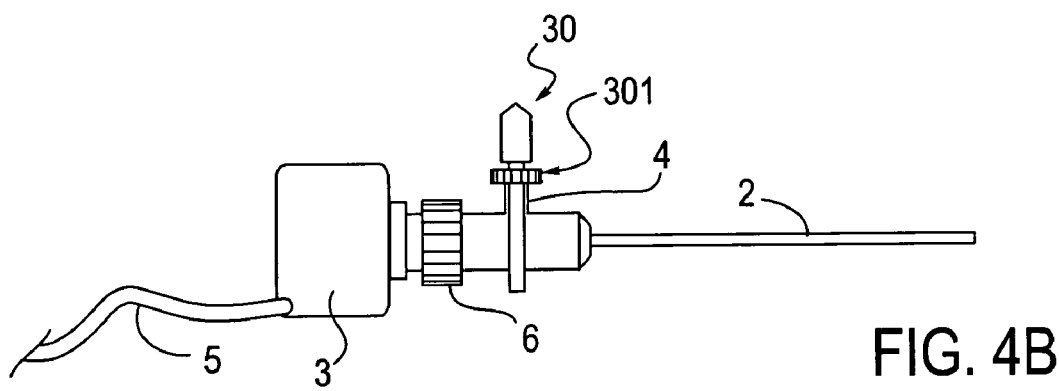
FIG. 4B shows a side view of an LED light source unit as described in FIG. 3 and an endoscope with the LED light source unit connected to the endoscope.

FIG. 4B shows a side view of the LED light source unit 30 and the endoscope 2 with the LED light source unit 30 connected to the endoscope 2. After the light source unit 30 is connected to the endoscope 2, light guide 204 (FIGS. 3A and 3B) of the light source unit 30 is coupled to a group of optical fibers running inside the endoscope 2 from the light post 4 to the tip of the endoscope 2. Thus, light produced by the LEDs 201 is filtered by the phosphor layer 202, collected by the light guide 204, coupled via the light post 4 into the optical fibers within the endoscope 2, and directed to the tip of the endoscope 2. Compared with supplying light from the conventional light source unit 7 (FIG. 1A), the present invention substantially reduces the distance the light must travel before reaching the surgical site; therefore, a lower-intensity light source, such as an LED array, can be used. This allows use of LEDs which operate on battery power and allows it to be made disposable.

Figure 4C:
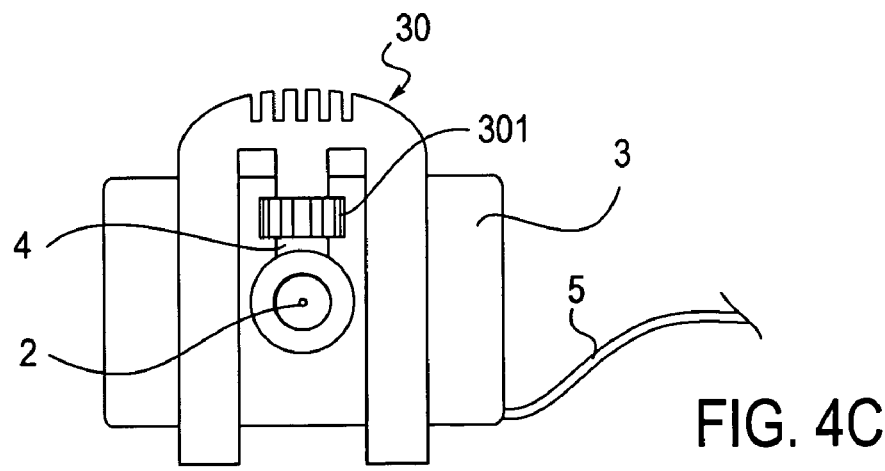
FIG. 4C shows a front view of an LED light source unit as described in FIG. 3 and an endoscope with the LED light source unit connected to the endoscope.

FIG. 4C shows a front view (orthogonal to FIG. 4B) of the LED light source unit 30 and endoscope 2 with the LED light source unit 30 connected to the endoscope 2. Note that FIG. 4C is not drawn to the same scale as FIGS. 4A and 4B.

Figure 5:
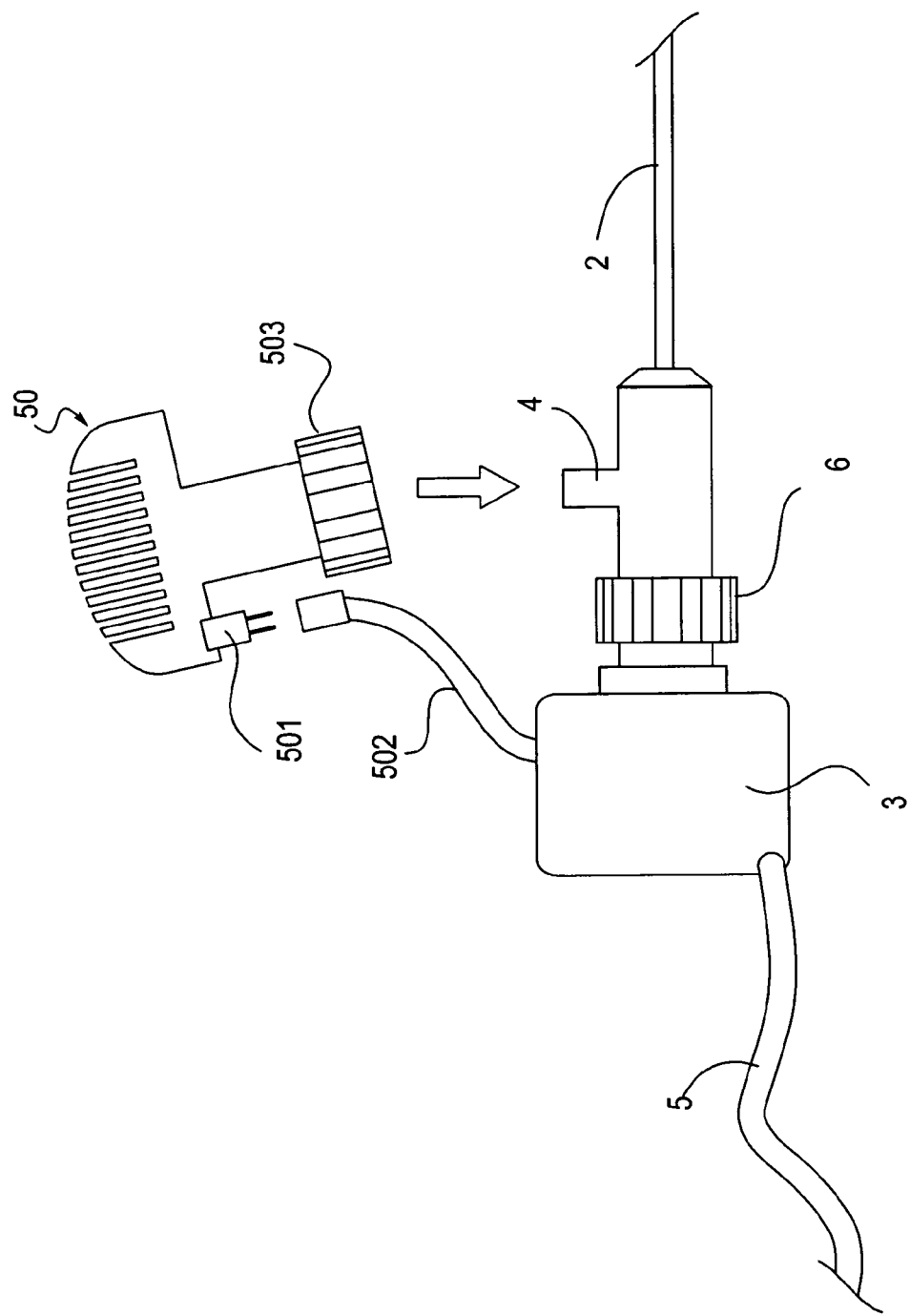
FIG. 5 shows an LED light source unit which is powered by a camera through a cable and which may be removably coupled to an endoscope.

FIG. 5 shows an LED light source unit powered by a camera through a cable, according to another embodiment of the invention. The light source unit 50, as shown, may be essentially the same as the LED light source unit 30 shown in FIG. 3A or 3B, except that connector 501 receives power through a cable 502 from a camera 3, rather than from batteries in the light source unit 30.

In a variation of the embodiment shown in FIG. 5, power is instead transmitted from the camera 3 to the endoscope 2, and then from the endoscope 2 to the LED light source unit 30 via contacts on the light post 4 that match contacts on the LED light source unit 30.

Note that although the different ways of supplying power to the LEDs (by battery or via transmission cable) are illustrated individually in different embodiments above, one can easily combine them in one embodiment so that a user can choose the preferred way of power supply in different situations.

Figure 6A:
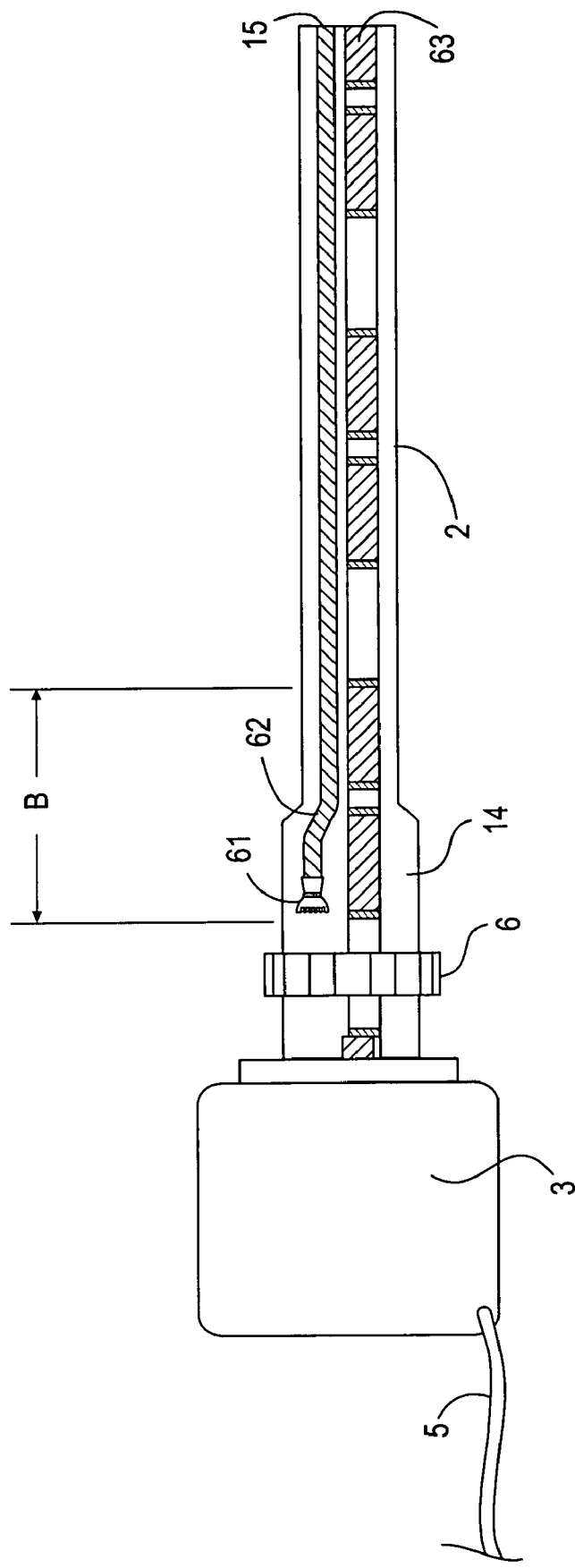
FIG. 6A illustrates an LED light source unit integrated into the proximal end of an endoscope.

FIG. 6A illustrates an LED light source unit integrated into an endoscope, according to yet another embodiment of the invention. As shown, the LED light source unit 61, similar to the one illustrated in FIG. 2, is integrated into the proximal end (the housing 14, for example) of an endoscope 2. Note that while only one light source unit 61 is shown in FIG. 6A, there can be more than one light source unit 61 integrated into the endoscope 2, such as one light source unit 61 to generate each of red, green and blue light.

Figure 6B:
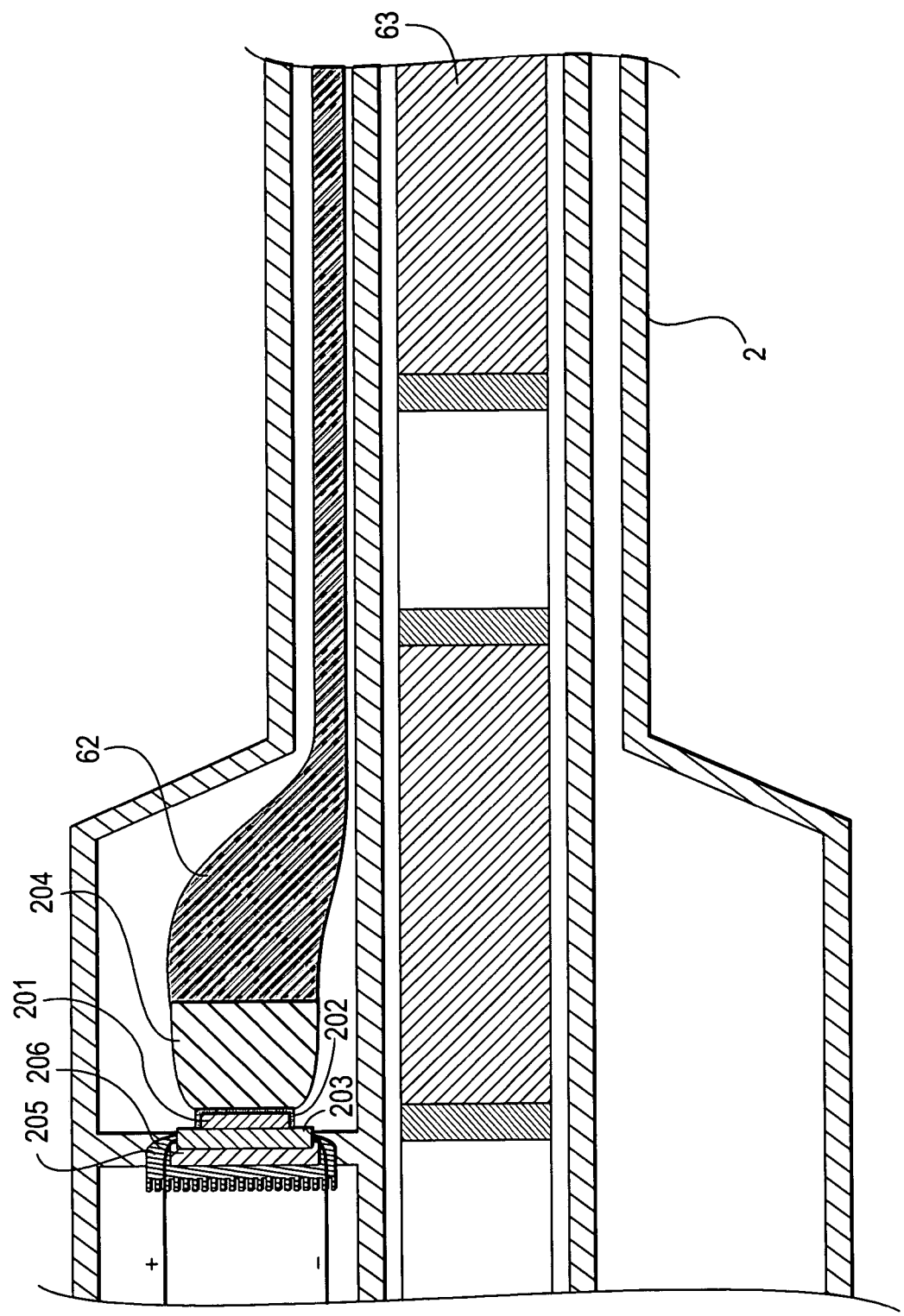
FIG. 6B shows a close up cross-sectional view of section B of FIG. 6A.

FIG. 6B is a close up view of section B in FIG. 6A and shows the light guide 204 directly coupled to a group of optical fibers 62 running to the distal end (the tip 15) of the endoscope 2 to provide illumination to the surgical site (optical epoxy can be used to bond the optical fibers 62 to the light guide 204). Since the amount of light required is fairly high and the relative brightness of the LEDs is low, the efficiency of the optical coupling between the light guide 204 and the optical fibers 62 is very high to reduce the losses when light travels through the coupling surface. Accordingly, unlike in the disposable embodiment described above, where more losses exist in coupling light through the light post 4, it is not necessary to overdrive the LEDs in this embodiment. Neither is it practical or economically desirable to make the light source unit 61 disposable, since it is integrated within the endoscope 2. The camera 3 acquires color video image data of internal features of a body through an optical pathway 63 (a system of lenses, for example) in the endoscope 2. Compared with the tip 15 or annular area of the scope shaft, the housing 14 can provide more space to hold more LEDs as a light source.

FIG. 6C shows a close up cross-sectional view of section B of FIG. 6A according to another embodiment, in which the substrate 203 is coupled to a heat sink 66 via a heat pipe 64 (shown in cross-section) integrated within the endoscope 2. More specifically, the substrate 203 is thermally coupled to the heat pipe 64 by a thermally conductive extension 65. The heat pipe 64 is thermally coupled to the heat sink 66, which is located distally from the substrate 203. Heat is transferred from the substrate 203 to the heat sink 66 via the thermally conductive extension 65 and the heat pipe 64.

The heat sink 66 can be a substantially doughnut-shaped structure (i.e., when the endoscope 2 is viewed end-on) which is coaxial with the longitudinal axis 68 of the endoscope 2 and which extends circumfrencially beyond the outer sheath 69 of the endoscope 2, as shown. Alternatively, the heat sink 66 can be square or another shape. The heat sink 66 may be monolithic or it may be formed from multiple discrete parts. The heat sink 66 further may include channels through which the optical fibers 62 and the lens system 63 can pass. The heat pipe 64 may be hollow tube filled with alcohol or another liquid, for example.

The heat pipe 64 may extend to the distal tip or the proximal side of the endoscope 2 where there is air circulation or another source of cooling.

Figure 6D:
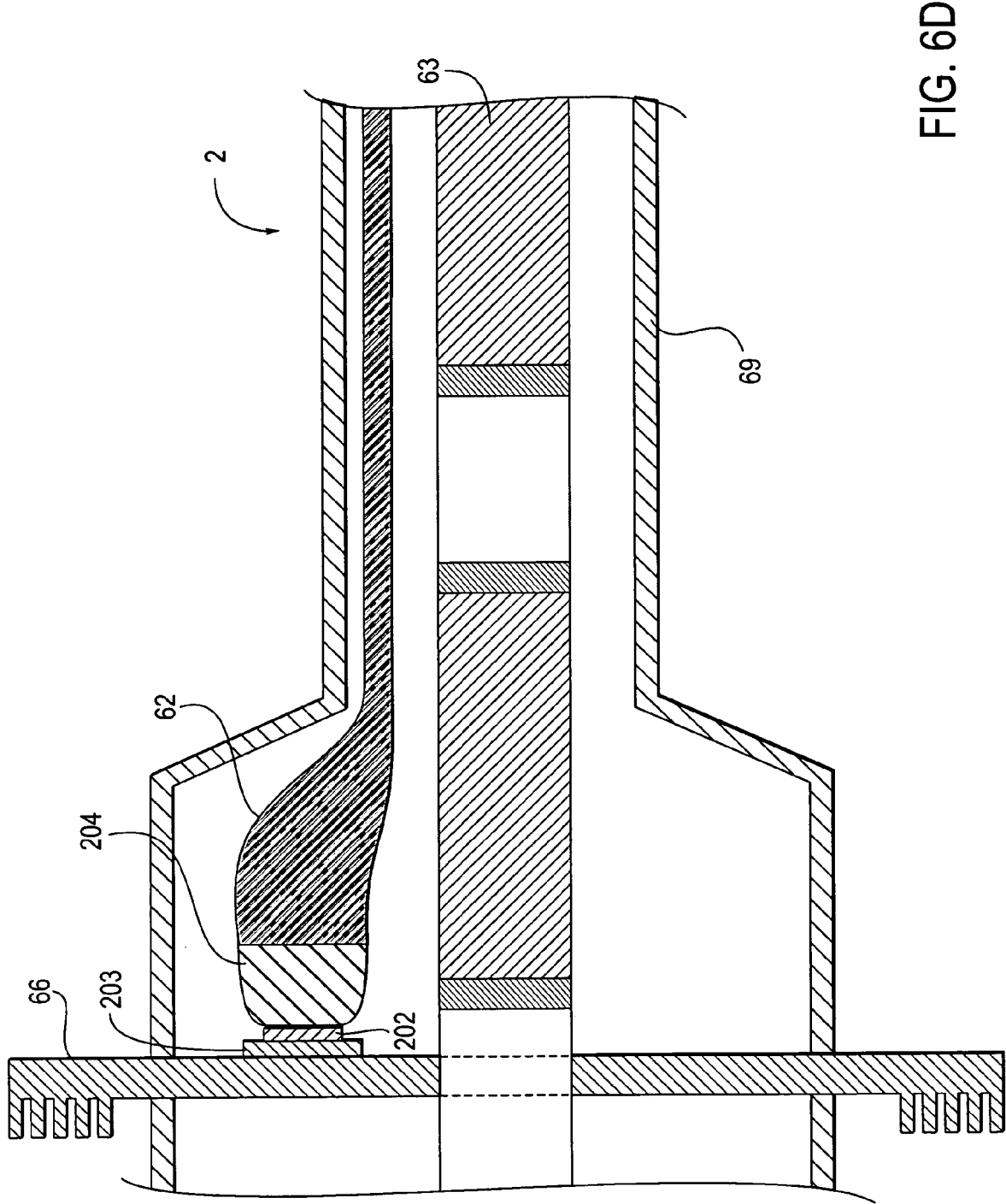
FIG. 6D shows a close up cross-sectional view of section B of FIG. 6A, for an embodiment in which a heat sink is connected directly to the substrate.

FIG. 6D shows yet another embodiment in which the heat sink 66 is connected directly to the proximal side of the substrate 203, without a heat pipe.

Figure 7A:
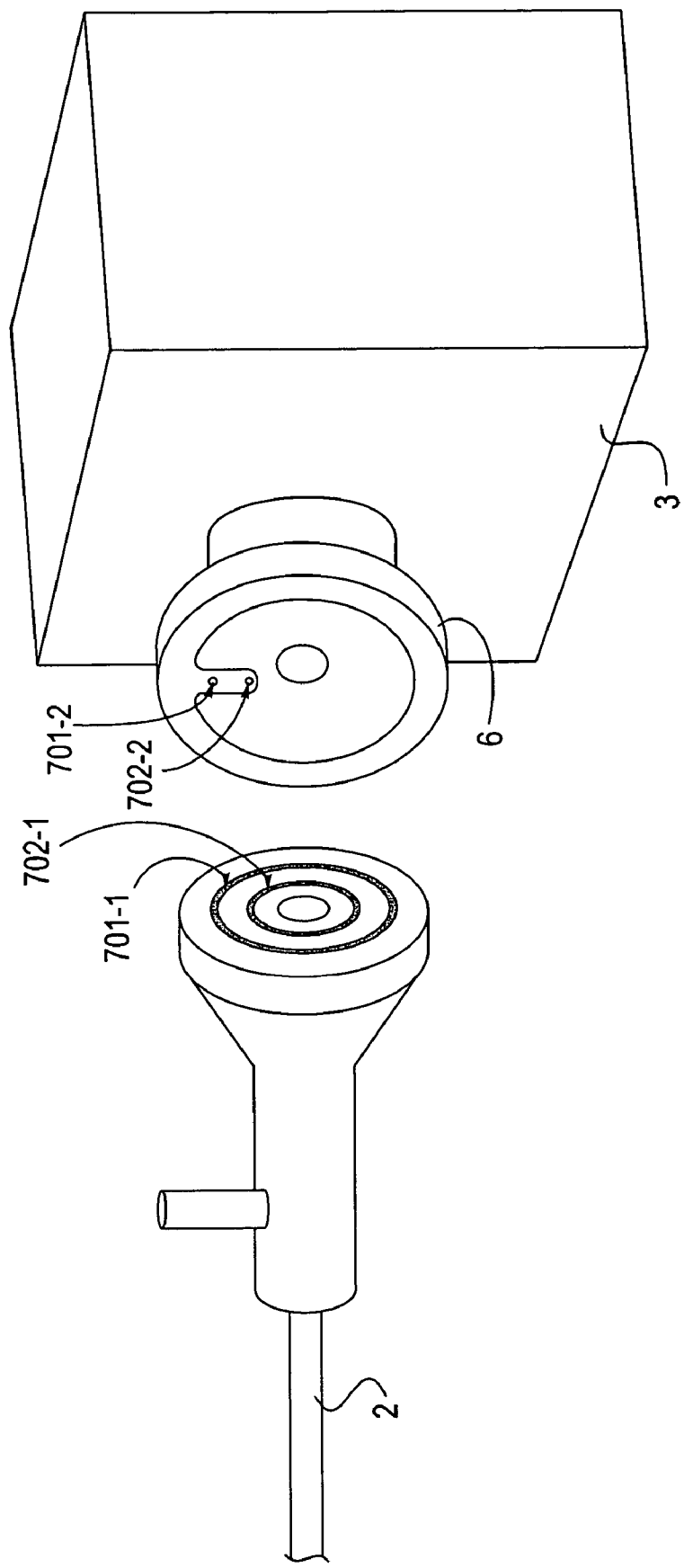
FIG. 7A illustrates a slip ring power connector to transmit power from a camera to an LED light source unit integrated into an endoscope.

FIG. 7A illustrates a technique for supplying power to the light source unit 61 in FIG. 6A. More specifically, FIG. 7A shows a slip ring power connector to transmit power from a camera to an LED light source unit integrated into an endoscope. A positive conductive ring terminal 701-1 and a negative conductive ring terminal 702-1 are placed at the proximal end of an endoscope 2, as shown, to contact respectively to a positive pin terminal 701-2 and a negative pin terminal 702-2 on a coupler 6 to transmit power from a camera 3 to the endoscope 2 for the LED light source unit 61 integrated therein. The circular configuration of the concentric ring terminals 701-1 and 702-1 allows the endoscope 2 to rotate within the coupler 6 while power is being transmitted from the camera 3.

FIG. 7B illustrates a configuration to supply power via a cable from the camera 3 to the LED light source unit 61 in FIG. 6A. As shown, a cable 704 can plug into a connector 703 of an endoscope 2 to transmit the DC power from the camera 3 to the LED light source unit 61. Also as shown, a battery pack 705 can replace the camera 3 as the source of power.

FIG. 7C illustrates a configuration to supply power wirelessly from the camera 3 to the LED light source unit 61 in FIG. 6A. A wireless power transmitter 706 is integrated with the camera 3 to transmit power to a wireless power receiver 707 integrated with the endoscope 2. The receiver 707 is wired to the LED light source unit 61 to supply the received power to the LEDs. The wireless power transmission technology used here could be, for example, inductive coupling. Note that the details of implementing wireless power transmission technology, such as may be employed here, are not germane to the present invention and are well within the knowledge of those skilled in the art. Therefore, it is not necessary to explain such technology in further detail here.

As mentioned above, by controlling light emitted from different sections of the scope tip, it is possible to control light output into different regions of a surgical site, so that the light level can be more balanced in the acquired image. FIG. 8A shows an arrangement of multiple LED light source units integrated into an endoscope to accomplish such a feature. An optical pathway 85 (a system of lenses, for example) in the endoscope 2 running straight from the distal end to the proximal end is omitted in FIG. 8A to make the figure easier to understand. As shown, four (4) LED light source units 81, 82, 83, 84, of the type introduced above, are integrated into the housing 14 of the endoscope 2. Power may be transmitted via a slip ring connector, a cable, or wirelessly as discussed earlier. Each light source unit 81, 82, 83, 84 is directly coupled to a separate corresponding group of optical fibers 810, 820, 830, 840, respectively, running to the tip of the endoscope 2. As shown in FIG. 8B (a front view of the tip of the endoscope 2), each group of optical fibers 810, 820, 830, 840 directs light emitted from the corresponding light source unit 81, 82, 83, 84 to a distinct section of the tip of the endoscope 2.

Since the endoscope 2 can rotate relative to the camera 3, in order to control the regional light emission, it is necessary to know how the endoscope 2 is positioned relative to the camera image. This could be accomplished by placing a small fiducial mark in the optical pathway 85.

Figure 8C:
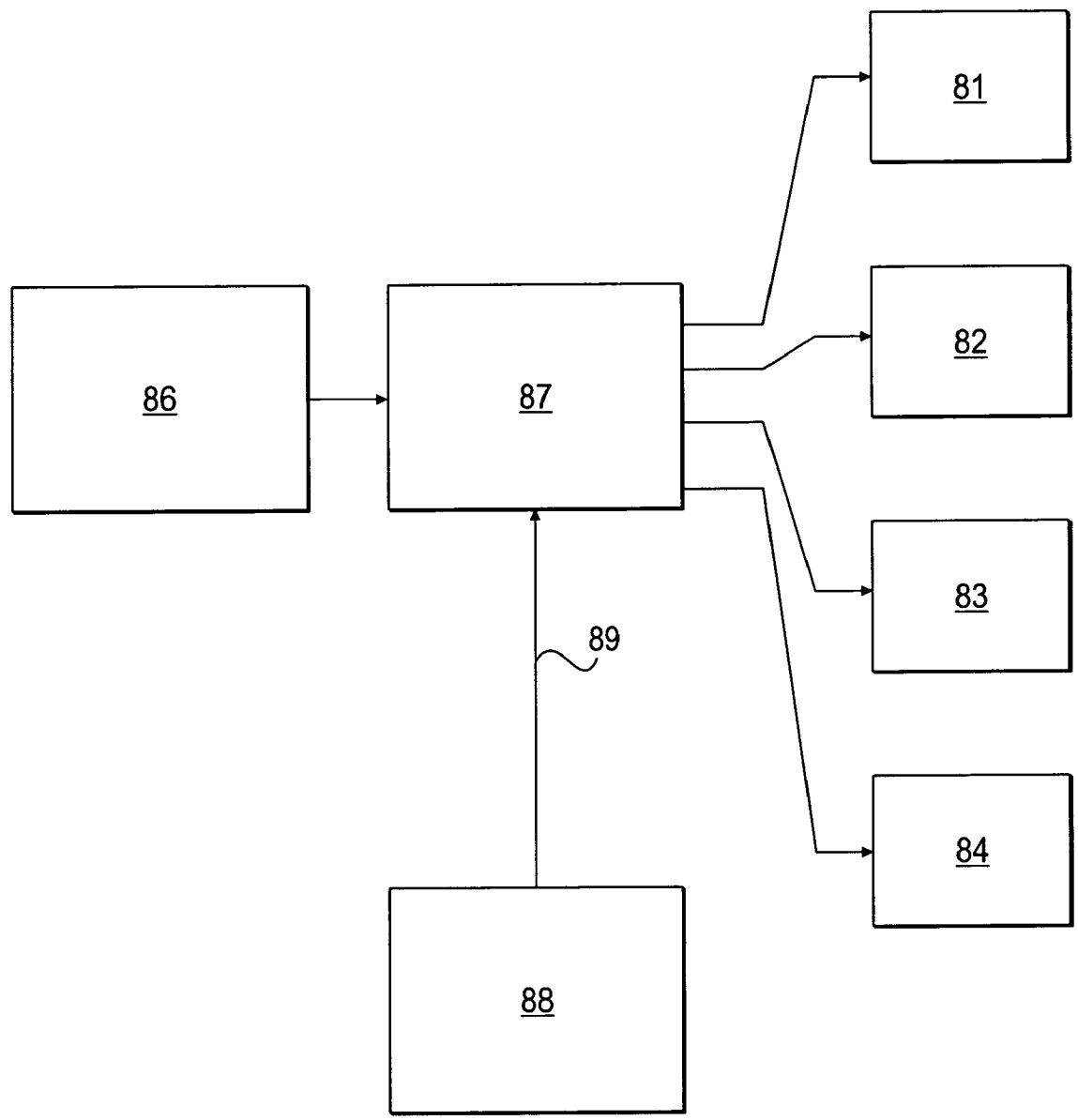
FIG. 8C is a block diagram illustrating a mechanism to control the light output of each individual LED light source unit integrated into an endoscope.

FIG. 8C is a block diagram illustrating a mechanism to control the light output of each individual LED light source unit integrated into an endoscope for the embodiment shown in FIGS. 8A and 8B. Switching circuitry 87 controls the power supplied from the power source 86 to each individual light source unit 81, 82, 83, 84, thereby controlling the light level output by each light source unit. A user controls an external control unit 88, e.g., a group of sliding bars, an electronic control panel, etc., which converts the user's control into signal 89 for the switching circuitry 87. The switching circuitry 87 then interprets the signal and carries out the operations intended by the user (increasing or reducing the light output of individual LED light source units, for example). Note that the external control unit 88 and the switching circuitry 87 may be implemented by any of various different techniques, e.g., mechanical, electrical, electronic, etc. Also note that, alternatively, each of the light source units may be made separately controllable by the user (a separate pair of switching circuitry and external control unit for each light source unit, for example). As such details are not germane to the present invention and are well within the knowledge of those skilled in the art, it is not necessary to explain them in further detail here.

Figure 9:
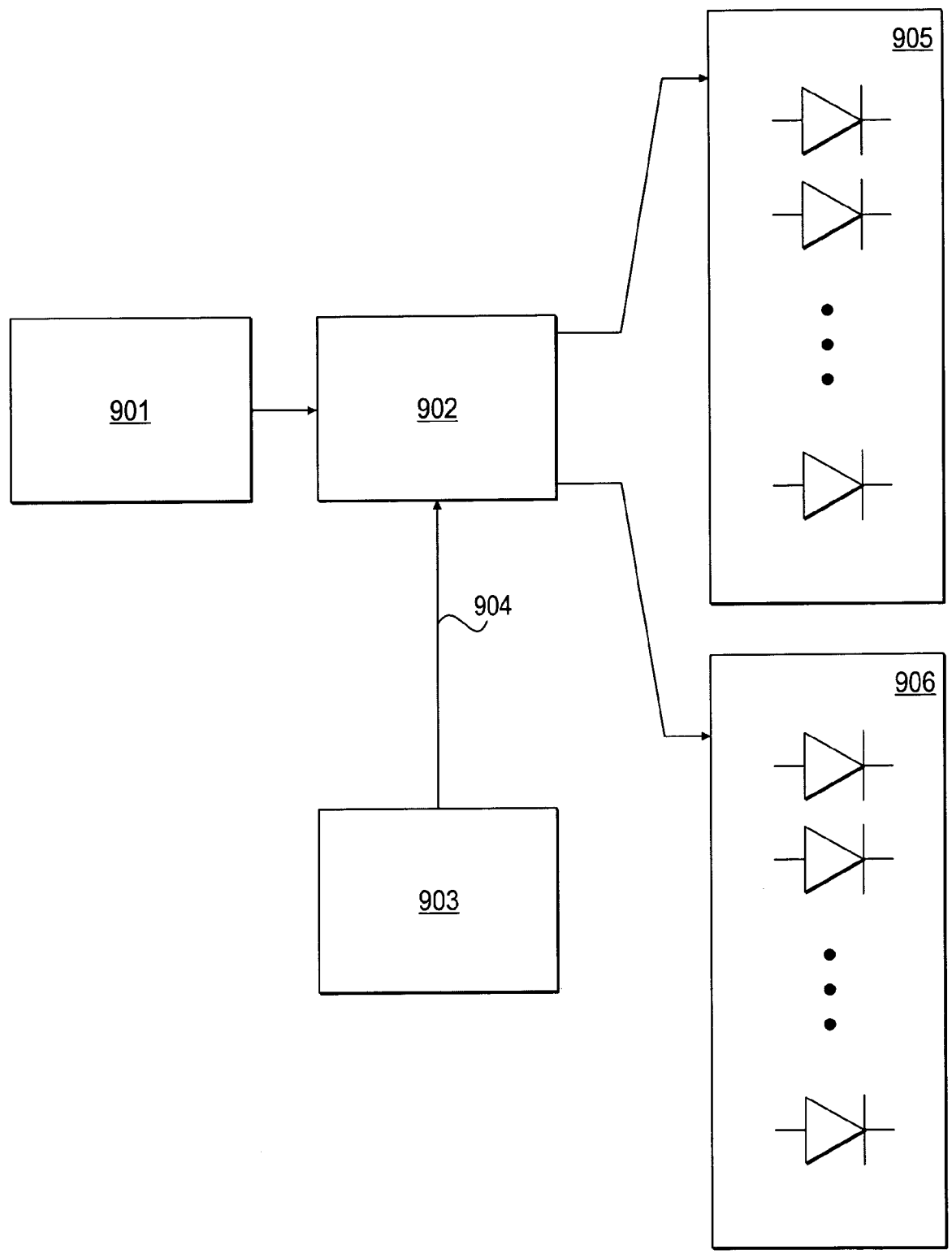
FIG. 9 is a block diagram illustrating the color temperature control mechanism of an LED light source unit.

FIG. 9 is a block diagram illustrating an example of the color temperature control mechanism, which may be applied to all embodiments described above. The array of LEDs of an LED light source unit may include a plurality of blue LEDs 905 and a plurality of red LEDs 906. Typically, for performance purposes, the number of red LEDs is smaller than the number of blue LEDs, and both the blue and red LEDs are distributed on a substrate as evenly as possible. For example, the blue and red LEDs can be distributed according to a matrix arrangement such that if the substrate is divided into many small square regions of the same size, each region contains relatively similar number of blue and red LEDs. A power source 901 supplies power to both the blue LEDs 905 and the red LEDs 906. The two groups of LEDs, however, are controlled separately by a switching circuitry 902, which may individually increase or decrease voltage and current delivered to the red group or the blue group and, accordingly, the amount of red light output or blue light output. A user may adjust the color temperature by operating an external control unit 903 (e.g., a sliding bar, an electronic control panel, etc.), which sends signals 904 to the switching circuitry 902. The switching circuitry 902 then interprets the signals 904 and carries out the operation intended by the user. This design has the functional result of changing the user-perceived color temperature of the light produced by the light source unit. Bluer light is considered "colder" and redder light is considered "warmer". Note that the external control unit 903 and the switching circuitry 902 may be implemented by any of various different techniques, e.g., mechanical, electrical, electronic, etc. Also note that, alternatively, the blue LEDs 905 and red LEDs 906 may be made separately controllable by the user (a separate pair of switching circuitry and external control unit for each group of LEDs, for example). As such details are not germane to the present invention and are well within the knowledge of those skilled in the art, it is not necessary to explain them in further detail here.

Thus, an LED based light source unit for an endoscopic imaging system has been described. Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. An apparatus comprising:
   an endoscope including a first optical pathway through which a camera acquires image data of internal features of a body; and
   a light source unit including
      a thermally conductive substrate;
      an array of LEDs mounted on the substrate, to produce illumination through the endoscope for a camera;
      a heat sink thermally coupled to a second side of the substrate via a heat pipe, wherein the heat pipe is a hollow metal tube filled with a liquid;
      a light guide to collect light emitted from the LEDs and couple the light along a more confined angle than as produced by the light emitting elements; and
      an interface adapted to removably mount the light source unit on an external light port of the endoscope, wherein the interface couples the light from the light guide directly, without need for a cable, into a second optical pathway within the endoscope via the external light port, wherein the second optical pathway directs the light to an distal end of the endoscope, wherein the interface is adapted to mount the light source unit on external light ports of endoscopes of a variety of different sizes and manufacturers, and wherein the interface enables the endoscope to bear the weight of the removably mounted light source unit.

2. An apparatus as recited in claim 1, wherein the light source unit further includes a layer of phosphor coated on the LEDs to control spectral content of emitted light from the LEDs.

3. An apparatus as recited in claim 1, wherein the light source unit further includes a battery to supply power to the LEDs.

4. An apparatus as recited in claim 1, wherein the light source unit further includes a connector to receive power via a cable from the camera to power the LEDs, the endoscope coupled to the camera.

5. An apparatus as recited in claim 1, wherein the LEDs are overdriven by power.

6. An apparatus as recited in claim 1, wherein the array of LEDs comprises a plurality of LEDs of a first color and a plurality of LEDs of a second color; and the light source unit further includes switching circuitry to control a color temperature of light emitted from the LEDs.

* * * * *